US007899542B2

(12) United States Patent  (10) Patent No.: US 7,899,542 B2
Cowan et al.  (45) Date of Patent: *Mar. 1, 2011

(54) SYSTEMS AND METHODS FOR IMPLANTABLE LEADLESS SPINE STIMULATION

(75) Inventors: Mark W. Cowan, Fremont, CA (US); Richard E. Riley, Palo Alto, CA (US); Axel F. Brisken, Fremont, CA (US); Debra S. Echt, Woodside, CA (US)

(73) Assignee: EBR Systems, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/764,574

(22) Filed: Jun. 18, 2007

(65) Prior Publication Data
US 2007/0293909 A1 Dec. 20, 2007

Related U.S. Application Data

(60) Provisional application No. 60/805,315, filed on Jun. 20, 2006.

(51) Int. Cl.
*A61N 1/372* (2006.01)
(52) U.S. Cl. .............................. 607/46; 607/61
(58) Field of Classification Search .................. 607/46, 607/61
See application file for complete search history.

(56) References Cited

U.S. PATENT DOCUMENTS

| 3,835,833 | A | 9/1974 | Limoge |
| 4,690,144 | A | 9/1987 | Rise et al. |
| 5,405,367 | A | 4/1995 | Schulman et al. |
| 5,938,690 | A | 8/1999 | Law et al. |
| 6,002,965 | A | 12/1999 | Katz et al. |
| 6,027,456 | A | 2/2000 | Feler et al. |
| 6,037,704 | A | 3/2000 | Welle |
| 6,366,816 | B1 | 4/2002 | Marchesi |
| 6,735,475 | B1 | 5/2004 | Whitehurst et al. |
| 6,748,276 | B1 | 6/2004 | Daignault, Jr. et al. |
| 2004/0172083 | A1* | 9/2004 | Penner ............................ 607/35 |
| 2006/0136004 | A1* | 6/2006 | Cowan et al. .................... 607/33 |

FOREIGN PATENT DOCUMENTS

DE 4330680 3/1995

* cited by examiner

*Primary Examiner* — Mark W Bockelman
*Assistant Examiner* — Eric D. Bertram
(74) *Attorney, Agent, or Firm* — Kilpatrick Townsend & Stockton LLP

(57) ABSTRACT

Systems and methods are disclosed to stimulate spine tissue to treat medical conditions such as pain and spinal injury. The invention uses electrical stimulation of the spine, where vibrational energy from a source is received by an implanted device and converted to electrical energy and the converted electrical energy is used by implanted electrodes to stimulate the pre-determined brain site. The vibrational energy is generated by a controller-transmitter, which could be located either externally or implanted. The vibrational energy is received by a receiver-stimulator, which could be located in the various regions on around the spine. The implantable receiver-stimulator stimulates different locations in the spine region to provide therapeutic benefit.

13 Claims, 6 Drawing Sheets

SYSTEMS AND METHODS FOR IMPLANTABLE LEADLESS SPINE STIMULATION

CROSS-REFERENCES TO RELATED APPLICATIONS

The present application claims the benefit of provisional U.S. Application No. 60/805,315, filed Jun. 20, 2006, the full disclosure of which is incorporated herein by reference.

BACKGROUND OF THE INVENTION

1. Field of the Invention

The systems and methods of this invention relate to direct electrical stimulation of nerve tissue in the spinal cord or spinal column for treatment of pain due to a variety of medical conditions. Specifically, the present invention relates to methods and apparatus for applying such stimulation without the use of conventional lead/electrode systems.

2. Description of the Background Art

Electrical stimulation of spinal nerve roots, the spinal cord, and/or other nerve bundles in the region of the spine, for the purpose of chronic pain management, has been actively practiced since the 1960s. Application of an electrical field to nerve tissue in the spine (i.e., spinal nerve roots and spinal cord bundles) is known to effectively interfere with the transmission of pain signals to the brain. These applications are done today both with externally applied devices and implanted devices. Applying specific electrical pulses to spinal nervous tissue or to peripheral nerve fibers that corresponds to regions of the body afflicted with chronic pain can induce paresthesia, or a subjective sensation of numbness or tingling, or can in effect block pain transmission to the brain from the pain-afflicted regions. Depending on the individual patient, paresthesia can effectively "mask" certain pain sensations to the brain. Treatment regimens and targeted spinal locations are known in related art through use of current, common stimulation devices and methods. Commonly implanted devices for spinal nerve stimulation are made by such companies as Medtronic, Advanced Neuromodulation Systems, Advanced Bionics, and others.

The spine is an anatomical structure that consists of bones (vertebrae), cartilage (discs), and the spinal cord (a nervous system structure that generally bundles or collects various nerves connecting peripheral areas of the body to the brain). As illustrated in FIG. 1 the spine is divided into five regions: (i) cervical (neck), (ii) thoracic (mid-back), (iii) lumbar (lower back), (iv) sacrum, and (v) coccyx (tailbone). The peripheral nervous system refers to the cervical, thoracic, lumbar, and sacral nerve trunks leading away from the spine to all regions of the body. The peripheral nervous system also includes cranial nerves. Pain signals travel between the brain and to other regions of the body using this network of nerves that all travel along the spine as part of the spinal cord.

Transcutaneous electrical nerve stimulation (TENS) is a well known medical treatment used primarily for symptomatic relief and management of chronic intractable pain and as an adjunctive treatment in the management of post surgical and post traumatic acute pain. TENS involves the application of electrical pulses to the skin of a patient, which pulses are generally of a low frequency and are intended to affect the nervous system in such a way as to suppress the sensation of pain, in the area that the electrodes are applied. This typically would be indicated for use in acute or chronic injury or otherwise used as a protective mechanism against pain. Typically, two electrodes are secured to the skin at appropriately selected locations. Mild electrical impulses are then passed into the skin through the electrodes to interact with the nerves lying thereunder. As a symptomatic treatment, TENS has proven to effectively reduce both chronic and acute pain of patients.

Spinal Cord Stimulation (SCS) generally refers to treatments for a variety of medical conditions that apply electrical stimulation directly on nerves, nerve roots, nerve bundles, tissue or regions of the spine. Currently available stimulator systems for SCS are fully implanted electronic devices placed subcutaneously under the skin and connected via insulated metal lead(s) to electrodes which are invasively inserted into or onto the nerves or close to the nerves or spinal cord region. A commonly implanted SCS system contains a battery to power the system. Some implanted SCS systems use an RF wireless connection instead of a battery to power the implanted device. In these RF systems, a receiver device is implanted subcutaneously and a transmitter is worn on the outside of the body. The antenna are tuned to each other and aligned such that control information and power is transmitted to the receiver, which then directs the electrical impulses to the electrodes through the leads. The external transmitter contains batteries to power the transmission. All systems have the capability to externally adjust settings of the implanted system through a programming device.

In SCS and TENS systems, electrical energy is delivered through lead wires to the electrodes. For SCS, implanted electrodes are positioned external to a patient's dura layer (epidural), a structure that surrounds the spinal cord. SCS uses the implanted electrodes to deliver a variety of stimulation modalities with the electric pulse waveform defined by a plurality of variables, including: pulse width, pulse frequency (Hz) or duty cycle, amplitude (V), and sometimes waveform shape (e.g. mono-phasic or bi-phasic).

SCS is used for treatment of headache, migraine headache, or facial pain by stimulating spinal cord including the trigeminal ganglion or ganglia, a trigeminal nerve(s), a branch(es) of a trigeminal nerve(s) (e.g., an ophthalmic nerve(s), a maxillary nerve(s), and/or a mandibular nerve(s)), or a branch(es) of any of these neural structures.

SCS is used for the treatment of chronic pelvic pain due to such conditions as lumbosacral radiculitis, lumbosacral radiculopathy, lumbosacral plexitis, lumbosacral plexopathy, vulvadynia, coccygodynia, peripheral neuritis, and peripheral neuropathy, by applying stimulation to the epidural space of the sacrum on or near selected sacral nerve roots.

SCS is used for chronic pain associated with injury to the spine such as herniated discs or compression fractures. SCS is also used for treating severe chronic pain of a nonspecific origin. Stimulation of nerve tissue in a variety of spinal areas is known to reduce symptoms and enhance the quality of life in patients with chronic pain.

As described above, TENS and SCS devices are battery-powered electronic devices either used transcutaneously (TENS) or implanted (SCS) and connected via insulated metal lead(s) to electrodes which are either placed on the skin (TENS) over the spine or implanted into the dura or epidural layer of the spine (SCS). The implanted electrodes for SCS are positioned on leads that are placed percutaneously, through needle punctures, or through minimally invasive surgical procedures such laminectomy methods, or through direct surgical access to position the electrodes into epidural regions of the spine. Multiple electrodes typically between 4 and 16 are available on the lead and are positioned in the region that is targeted for electrical stimulation. The implanted leads are then subcutaneously tunneled to the pulse generator (also referred to as a controller) that is implanted in a subcutaneous pocket. The use of these lead wires is associated with significant problems such as complications due to infection, lead failure, lead migration, and electrode/lead dislodgement.

Many attempts to overcome the complications and limitations imposed by the use of electrical leads have been reported. For example, self-contained implantable microstimulators and remotely powered microstimulators have been described; however each approach suffers from some significant limitation. A self-contained microstimulator must incorporate a battery or some other power supply; this imposes constraints on size, device lifetime, available stimulation energy, or all three. Due to high use or high energy requirements of the therapeutic stimulation some SCS devices contain rechargeable batteries or are powered remotely with an RF coupling to the controller.

For leadless solutions in other similar stimulation applications, remotely powered devices have previously utilized either radiofrequency (RF) or electromagnetic transformer power transmission. RF energy transmission, unless the transmitting and receiving antennae are placed in close proximity, suffers from inefficiency and limited safe power transfer capabilities, limiting its usefulness in applications where recharging or stimulation must be accomplished at any significant depth (>1-2 cm) within the body, in particular where it is desired to permanently implant both the transmitter and receiver-stimulator. Electromagnetic coupling can more efficiently transfer electrical power, and can safely transfer higher levels of power (devices with capacity in excess of 20 Watts have been produced) but again relies on close proximity between transmitting and receiving coils, or the utilization of relatively large devices for deeper (5-8 cm maximum) implantation.

The methods and apparatus of the current invention utilize vibrational energy, particularly at ultrasonic frequencies, to overcome many of the limitations of currently known solutions for SCS and TENS, by achieving a spinal cord stimulation capability without the use of leads connected to a stimulation controller/pulse generator.

The following patents, all of which are incorporated in this disclosure in their entirety, describe various aspects of using electrical stimulation for achieving various beneficial effects. U.S. Pat. No. 3,835,833 titled "Method for Obtaining Neurophysiological Effects" by Limoge describes delivery and parameters for electrical stimulation in a TENS stimulation system. U.S. Pat. No. 4,690,144 titled "Wireless Transcutaneous Electrical Tissue Stimulator" by Rise et al. also describes delivery, systems, and application parameters for a TENS stimulation system. U.S. Pat. No. 6,735,475 titled "Fully implantable miniature neurostimulator for stimulation as a therapy for headache and/or facial pain" by Whitehurst et al. describes an implantable microstimulator used for treatment of pain in peripheral nerves generally in the skull or the cervical regions of the spine. U.S. Pat. No. 6,748,276 titled "Neuromodulation therapy system" by Daignault et al. describes an implantable SCS system that uses an external RF communication to adjust delivery of therapy. U.S. Pat. No. 6,027,456 titled "Apparatus and method for positioning spinal cord stimulation leads" by Feler et al. describes approaches to the implantation of leads into the dorsal column of a patient. U.S. Pat. No. 5,938,690 titled "Pain management system and method" by Law et al. describes methods for determining and optimizing treatment parameters and regimens for by mapping patient responses to test stimulation patterns. U.S. Pat. No. 6,002,965 titled "Epidural nerve root stimulation" by Feler et al. describes treating pelvic pain by application of stimulation in the sacral and lumbar regions of the spine. U.S. Pat. No. 5,405,367 titled "Structure and Method of Manufacture of an Implantable Microstimulator" by Schulman et al. describes an implantable microstimulator used generally for stimulation of tissue. U.S. Pat. No. 6,037,704 titled "Ultrasonic Power Communication System" by Welle describes the use of ultrasound energy transfer from a transmitter to a receiver for purposes of powering a sensor or actuator without being connected by a lead/wire. U.S. Pat. No. 6,366,816 titled "Electronic Stimulation Equipment with Wireless Satellite Units" by Marchesi describes a tissue stimulation system based on a wireless radio transmission requiring the charging of a battery at the receiver and separate command signals used to control the delivery of stimulation. German patent application DE4330680A1 titled "Device for Electrical Stimulation of Cells within a Living Human or Animal" by Zwicker describes a general approach to power transfer using acoustic energy for tissue stimulation.

BRIEF SUMMARY OF THE INVENTION

This invention relates to methods and devices for using electrical stimulation of spinal cord nerves and regions of the spinal cord as a treatment for pain, particularly chronic pain using vibrational energy as a means to transmit energy and signal information from a first device, to a second device containing means to receive such vibrational energy and converting it into electrical energy and then apply that electrical energy to stimulating electrodes. The first device is intended to be either implanted or to be used externally. The second device is intended to be either permanently or temporarily implanted with stimulating electrodes in close proximity to the tissue or nerve region to be stimulated.

This application of leadless electrical stimulation is for spinal cord stimulation purposes, where the stimulation acts on the nerves to reduce pain. The invention is a system comprising a controller-transmitter, an implanted receiver-stimulator, a programmer to adjust therapy parameters, and stimulation electrodes, such that the stimulation electrodes would be in contact with tissue in the spine regions, in close proximity to the tissue or region to be stimulated to facilitate treatment. Systems incorporating the concepts presented have advantages over currently available devices, particularly by eliminating the requirement for electrical leads, and by providing the capability for simultaneous or sequenced stimulation of multiple sites.

In one embodiment, the controller-transmitter is implanted. The controller-transmitted is implanted subcutaneously beneath the skin. In another embodiment, the controller-transmitter is applied on the external surface of the skin. The transmitted vibrational energy is directed to the receiver-stimulator to cause electrical stimulation at the electrodes of the receiver-stimulator.

In one use of the external embodiment of the controller-transmitter, the device is for pain management of recurring but not continuous pain, for example, headache pain. In the external embodiment, miniaturized receiver-stimulator devices are implanted, but the controller-transmitter unit is external to the body, possibly hand-held or worn attached to a belt or harness. The acoustic energy from the external controller-transmitter is coupled through the skin as well as any underlying tissues, to the implanted device. The external controller-transmitter is under control of the patient. Thus, when the patient begins to feel pain, the controller-transmitter unit is applied and/or switched on, and certain characteristics, for example, the level of stimulating energy and possibly the frequency or pulse duration of the stimulating waveform, is modified by the user, enabling the user to tailor the stimulation as needed to diminish the pain.

DETAILED DESCRIPTION OF THE INVENTION

Figure 1:
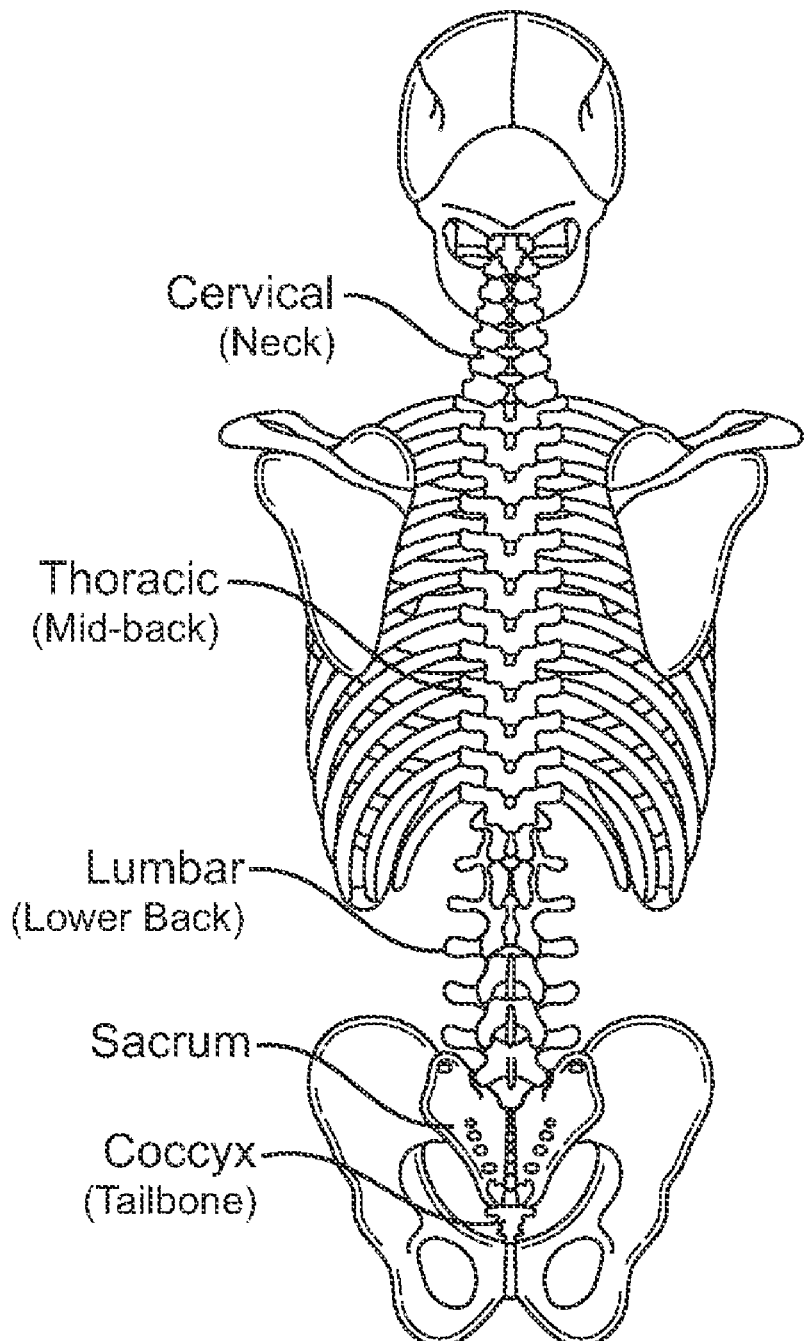
FIG. 1 is a schematic showing the basics of the spinal cord anatomy.

The systems and devices described here comprise a controller-transmitter device that will deliver vibrational energy and signal information to one or more implanted receiver-stimulator device(s) that will convert the vibrational energy to electrical energy of a form that can be used to electrically stimulate nerve tissue in the spine. The vibrational energy can be applied with ultrasound as a single burst or as multiple bursts or as a continuous wave with appropriate selection of the following parameters:

| Parameter | Value Range |
| --- | --- |
| Ultrasound frequency | 20 kHz-10 MHz |
| Burst Length (#cycles) | 3-Continuous |
| Stimulation Pulse Duration | 0.1 μsec-Continuous |
| Duty Cycle | 0-100% |
| Mechanical Index | ≦1.9 |

The controller-transmitter device would contain an ultrasound transducer or transducers of appropriate size(s) and aperture(s) to generate sufficient acoustic power to achieve the desired stimulation at the location of an implanted receiver-stimulator device. Additionally, multiple implanted receiver-stimulator devices may be placed within the region insonified by the controller-transmitter device. Multiple receiver-stimulator implants may function simultaneously; it is also possible for multiple devices to function independently, either by responding only to a specific transmitted frequency, or through the use of a selective modulation technique such as pulse width modulation, or through encoding techniques such as time-division multiplexing.

A leadless pulse stimulator would be applied as follows. Using a percutaneous needle delivery technique that is used to access the epidural space, a miniaturized receiver-stimulator device disposed within the delivery needle is implanted into tissue or attached to the desired location in the epidural space. Various techniques and tools for spinal access and probing of nerve tissue are commonly known. These could be adapted to facilitate delivery of the receiver-stimulator to these locations; the receiver-transmitter may incorporate means to provide permanent attachment to the implant site including possibly helical coils, barbs, tines, or the like. Alternatively, the receiver-stimulator could be implanted during a minimally invasive surgical procedure or an open spine surgical procedure.

Functionally, the receiver-stimulator device comprises an ultrasound transducer to receive acoustic energy and transform it into electrical energy, an electrical circuit to transform the alternating electrical energy into a direct current or a pre-determined waveform, and electrodes to transfer the electrical field energy between an electrode pair to the tissue and to the surrounding area.

Additionally, a controller-transmitter device is adapted for directional, vibrational energy transmission emitted by the device to intersect the implanted receiver-stimulator. In an implanted version, the controller-transmitter device containing the transmitting transducer is implanted typically just beneath the skin in a subcutaneous space. If not implanted, the transducer portion of the transmitter would be placed over the skin directionally angled to the target region containing the receiver-stimulator with acoustic gel, or other means, used for coupling the acoustic energy to the skin.

In an alternative embodiment, the controller-transmitter device is incorporated into a device also providing conventional lead-based electrical stimulation, in a spinal cord stimulation system, wherein a conventional lead/electrode system would provide stimulus to directly connected regions of the spine using leads and transmitting vibrational energy to provide stimulation to regions of the spine where receiver-stimulators are implanted.

The controller-transmitter device would contain similar elements of most currently available stimulator systems including a power source, stimulation control and timing circuitry, physiologic sensing systems; in the implanted embodiment, a system to communicate with an outside console for data transmission, diagnostic, and programming functions typically through a radiofrequency (RF) link is provided. Additionally, the controller-transmitter device would contain an ultrasound amplifier and one or more ultrasound transducers to generate acoustic energy, and transmit such energy in the general direction of the receiver-stimulator implanted in the spine region. The duration, timing, and power of the acoustic energy transmission would be controlled as required, per tested parameters that are constructed for specific treatments for pain.

A single receiver-stimulator device is implanted in the epidural region of the spine as described above for single-region stimulation; alternatively it would be possible to implant a plurality of receiver-stimulator devices to stimulate either simultaneously by receiving the same transmitted acoustic energy or independently by responding only to acoustic energy with specific characteristics (i.e., of a certain frequency, amplitude, or by other modulation or encoding of the acoustic waveform) intended to energize only that specific device. This enables a much more robust utilization of site and region specific stimulation, which is not currently practical with current lead-based implementations whose electrode spacing is fixed on the lead set selected for use. Selecting multiple sites and regions for treatments would be greatly enhanced by eliminating the need to connect multiple electrode sites to the stimulation energy source by the use of multiple leads/wires connected to the electrodes or by attempting to anticipate the required spacing between electrodes.

These examples are representative but in no way limiting of the applications in which an electro-acoustic stimulator may be utilized in this invention to stimulate tissue in the spine to effect treatment of pain.

The delivery of ultrasound energy and, therefore, electrical stimulation could either be automatically triggered based on information received from an internal or external physiological sensor, or be based upon programmed settings, or be manually activated by the patient or other individuals. More specifically, the timing of the initiation of the delivery and/or the duration of the delivery and/or the energy content of the delivery and/or the information content of the delivery could be based upon sensor information or based upon programmed settings or be manually controlled.

Figure 2:
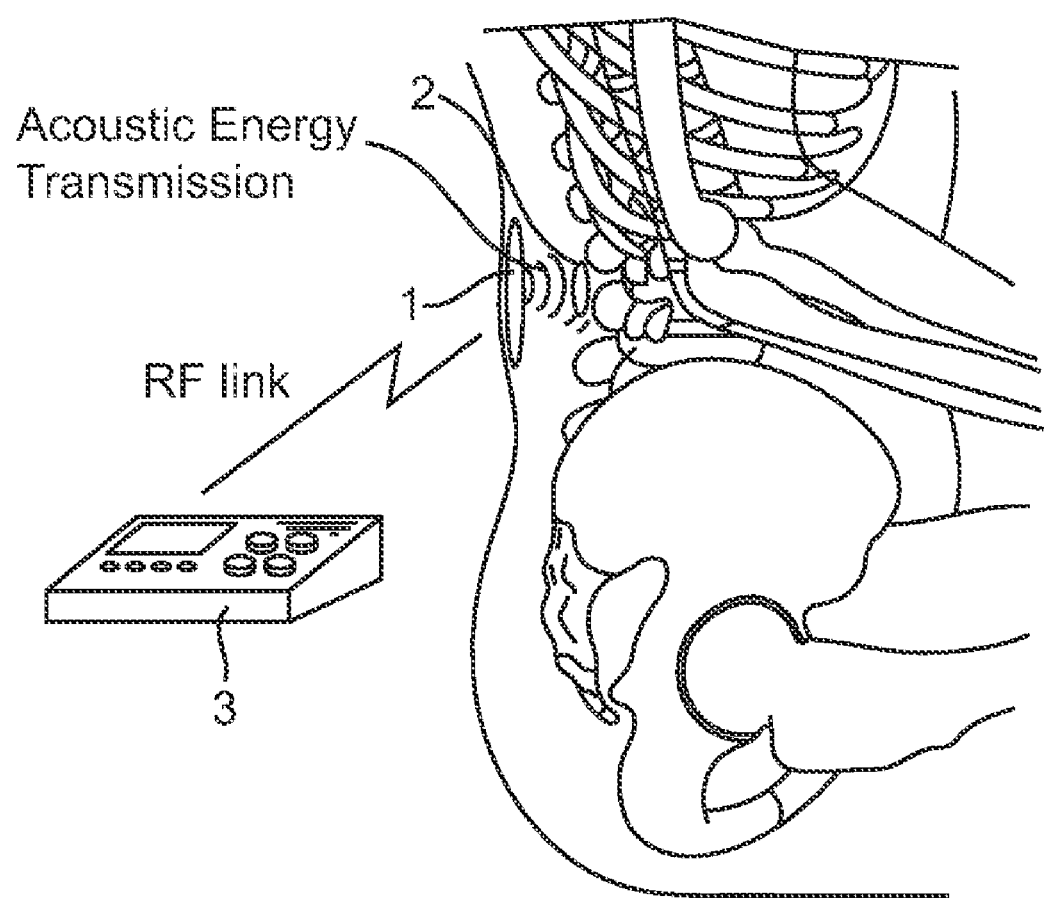
FIG. 2 is a schematic showing the leadless stimulation system in application with an implantable transmitter-controller for spinal cord stimulation.
Figure 3:
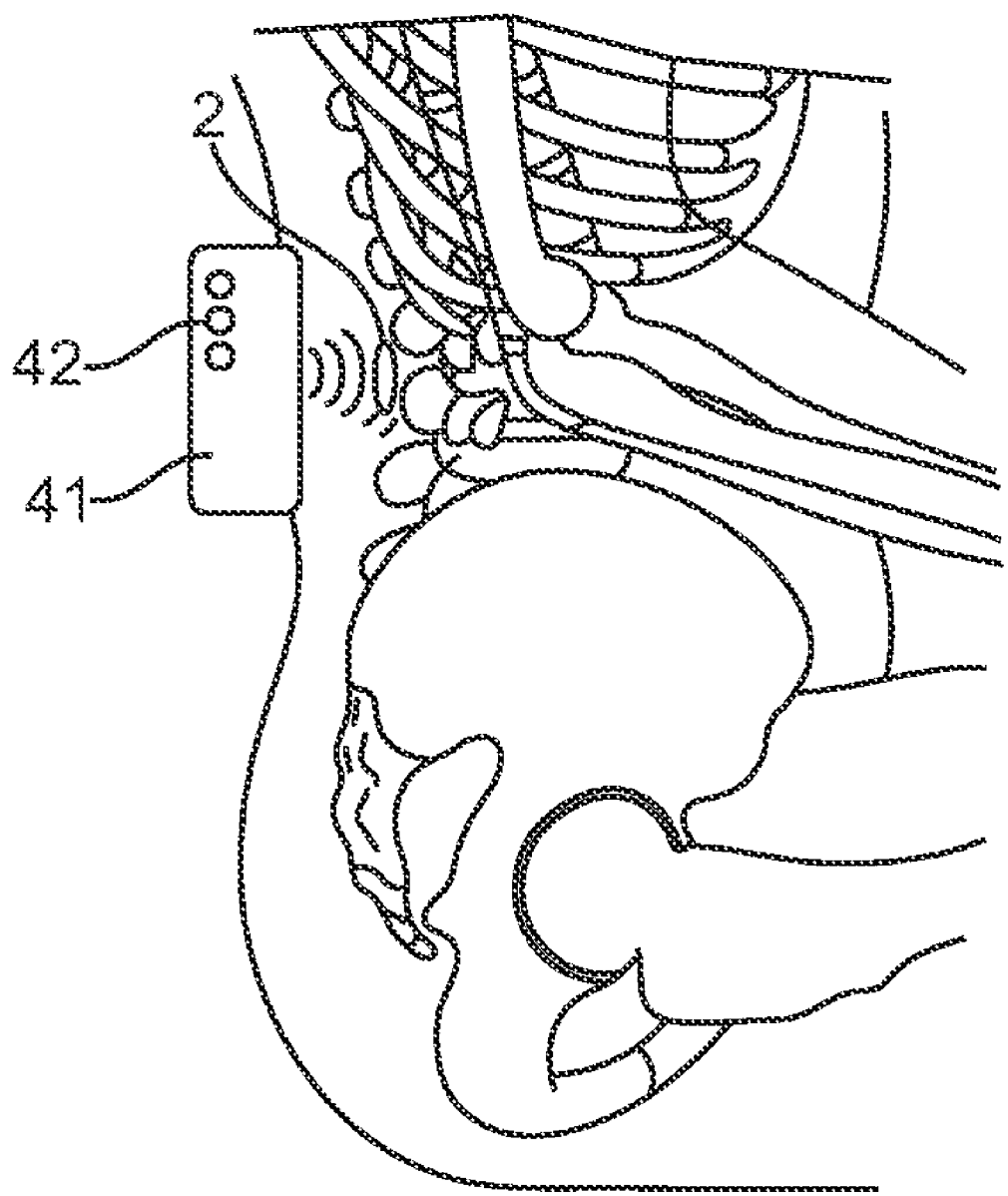
FIG. 3 is a schematic showing the leadless stimulation system in application with an externally applied transmitter-controller for spinal cord stimulation.

Examples of such an electro-acoustic stimulation system as a spine stimulator are illustrated in FIGS. 2 and 3.

In FIG. 2, a controller-transmitter device 1 containing circuitry to provide stimulation control and ultrasound transmission, plus means to communicate with an outside programmer 3 is implanted subcutaneously. It is situated such that the directional angle of the transmitted ultrasound beam would intersect the receiver-stimulator 2. An ultrasound signal is transmitted by this device through intervening tissue to the receiver-stimulator device 2 containing means to receive this acoustic energy and convert it into an electrical waveform which may then be applied to the attached electrodes. In FIG. 2, this receiver-stimulator device 2 is shown embedded, in this one example, in the lumbar region of the spine. The receiver-stimulator device 2 is shown here as a small cylindrical or button-shaped device placed in the epidural region similar to current stimulator systems. Optionally, the receiver-stimulator 2 could be deployed into the epidural space affixed with an attaching coil or other method. Also optionally (not shown), the receiver-stimulator device 2 could be incorporated into a expandable or self-expanding mechanical mesh that would stay located in the tissue by means of spring tension similar to a stent placement in a vascular application but rather held in place between tissue sections of the spine.

In FIG. 3, an externally applied controller-transmitter device 41 containing circuitry to provide stimulation therapy control and ultrasound transmission, plus control means 42 to allow the patient or operator to directly adjust ultrasound output based on desired therapy parameters including, at least, amplitude, pulse duration, and pulse repetition frequency, to produce effective pain relief. The external transmitter 41 may be handheld, or worn on the body, attached by a belt, harness, or the like. The external controller-transmitter 41 is similar to the implantable controller-transmitter device described previously, containing at the minimum an adjustable pulse/frequency generator, ultrasound amplifier, ultrasound transmitter, and battery. Optionally, the battery may be a rechargeable type. It is situated such that the directional angle of the transmitted ultrasound beam would intersect the receiver-stimulator 2. An ultrasound signal is transmitted by this device through intervening tissue to the receiver-stimulator device 2 containing means to receive this acoustic energy and convert it into an electrical waveform which may then be applied to the attached electrodes. In FIG. 3, this receiver-stimulator device 2 is shown embedded, in this one example, in the lumbar region of the spine.

Figures 4A, 4B:
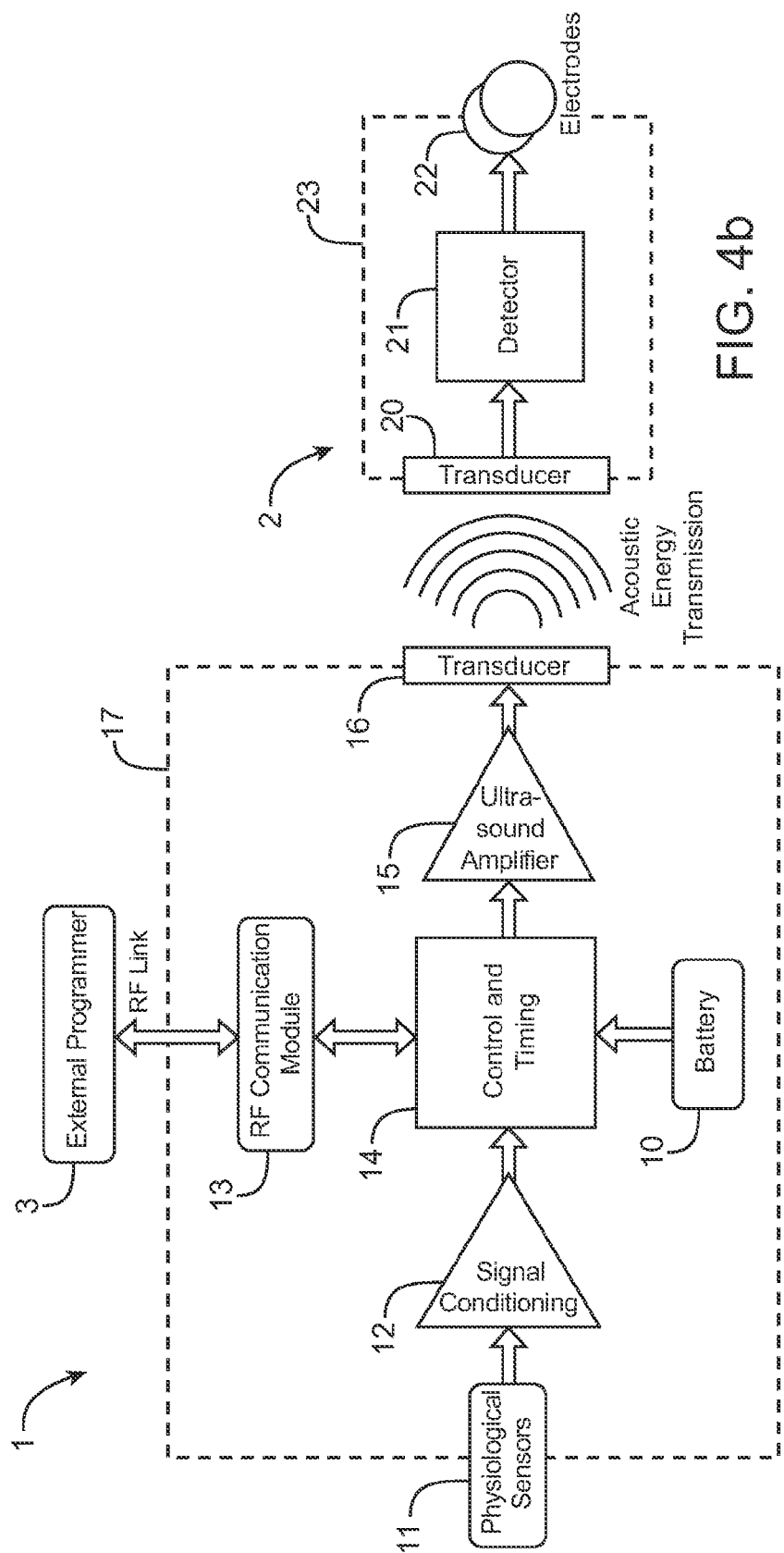
FIGS. 4a and 4b are block diagrams showing the components of the acoustic controller-transmitter and acoustic receiver-stimulators of the present invention.

FIGS. 4a and 4b show more details of the system described above and shown in FIG. 2. In FIG. 4a, the controller-transmitter device 1 comprises: a battery 10, one or more sensors 11, signal processing circuitry 12, a communications module 13, a control and timing module 14, an ultrasound amplifier 15, and an ultrasound transducer 16. The battery 10 which provides power for the controller-transmitter may be of a type commonly used in implanted medical devices such as a lithium iodine cell or lithium silver vanadium oxide cell made by Greatbatch, Inc. or which is optionally a rechargeable battery. One or more sensors 11 are used to detect physiological parameters. Suitable sensors are known for the detection of electrical activity, temperature, motion, pressure, and the like. These sensors are connected to signal processing circuitry 12 and optionally used by the circuitry to adjust delivery of stimulation therapy or to communicate diagnostic information from the sensors. The communications module 13 provides a data path to allow the physician to set device parameters and to acquire diagnostic information about the patient and/or the device. The data path may be by an RF communication link, magnetic coupling, ultrasound pulses, or the like, and would communicate to and from an external unit 3. Device parameters would be used by the control and timing module 14. Device parameters would include adjustments to transmissions, such as power amplitude, pulse duration, duty cycle, and the like. The control and timing module 14 uses device parameters in conjunction with the acquired physiological data to generate the required control signals for the ultrasound amplifier 15, which in turn applies electrical energy to the ultrasound transducer 16, which in turn produces the desired acoustic beam. The controller-transmitter device 1 is encased in a hermetically sealed case 17 constructed of a bio-compatible material, similar to current SCS devices.

Figure 5:
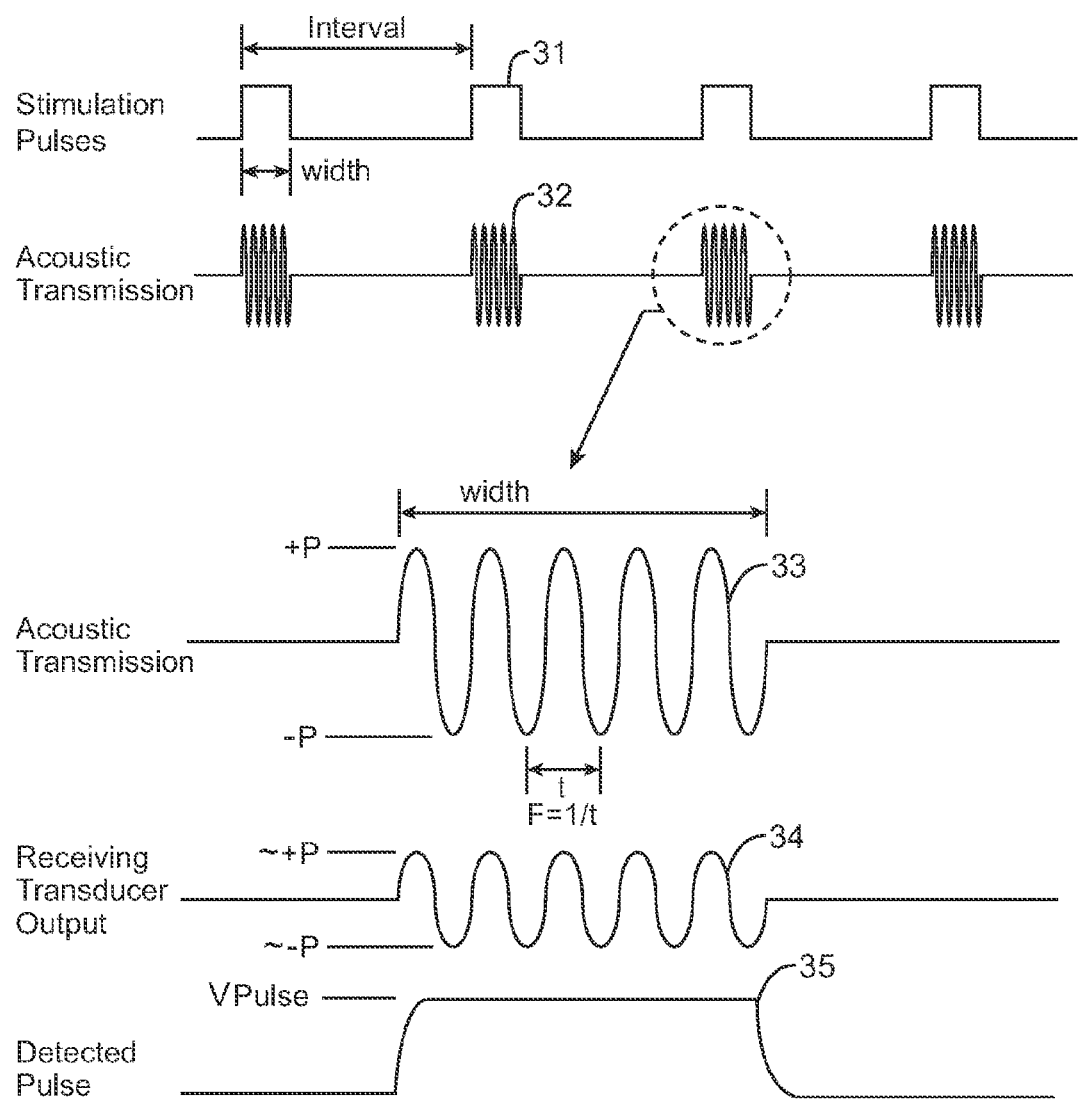
FIG. 5 illustrates representative acoustic and electrical signals useful in the systems and methods of the present invention.

Referring to FIG. 4b, the receiver-stimulator device 2, implanted in the path of the acoustic beam at the location where electrical stimulation is desired, contains an ultrasound transducer 20, an electrical circuit 21, and electrodes 22. Ultrasound transducer 20, typically made of a piezoelectric ceramic material, a piezoelectric single crystal, or piezoelectric polymer or copolymer films, intercepts a portion of the transmitted acoustic energy and converts it into an electrical current waveform from the original alternating nature of the applied ultrasound pressure wave. This electrical signal is applied to an electrical circuit 21 which may be one of a type commonly known as an envelope detector, and which may have one of many known circuit configurations; for example, a full-wave rectifier, a half-wave rectifier, a voltage doubler or the like. Electrical circuit 21 produces a voltage pulse with amplitude proportional to the amplitude of the transmitted ultrasound burst and with a pulse length generally equal to the length of the transmitted burst. The circuit 21 may also have different configurations and functionalities, and provide output signals having characteristics other than a pulse. This signal is then applied to electrodes 22, which are typically made of platinum, platinum-iridium, gold, or the like. These may be incorporated onto the outer surface of the device, and thus in direct contact within the epidural layer or within close proximity of nerves or nerve fibers which are to be treated by stimulation. Alternatively, the electrodes 22 are connected via wires to a main body that consists of the transducer 20 and electrical circuit 21 and the electrodes 22 are adapted to be shapeable, malleable configurations that conform to regions of the spine as flexible wraps or the like or that could be placed on the dura. Electrodes may be adapted that are round, long, segmented, etc. to increase surface area or to control current density at the electrode. Electrodes may be placed on opposing sides of the tissues or in linear alignment with the tissue or in any arrangement suitable for the size and location of the spine and the targeted spine stimulation site. The receiver-stimulator device 2 is also enclosed within a sealed case 23 of biologically compatible material Referring also to previously described FIGS. 4a and 4b, FIG. 5 provides detail representing exemplary acoustic and electrical signals of the present system. FIG. 5 first depicts a train of electrical stimulation pulses 31 which have a desired width and are repeated at a desired interval. The controller-transmitter device 1 produces acoustic transmissions 32, for the desired stimulation pulse width and repeated at the desired stimulation pulse interval, which are emitted from the ultrasound transducer 16. Below the waveform 32 is shown an enlargement 33 of a single acoustic burst. This burst again has a desired width, a desired oscillation frequency F=1/t, and also a desired acoustic pressure indicated by the peak positive pressure P+ and peak negative pressure P−. The acoustic pressure wave, when striking the receiving transducer 20 of the receiver-stimulator device 2 generates an electrical signal 34 having frequency and burst length matching that of the transmitted waveform 33 and amplitude proportional to the transmitted acoustic pressure (∼+/−P). This electrical waveform is then rectified and filtered by the circuit 21 producing the desired pulse 35 with length equal to the burst length of the transmitted waveform 33 and amplitude ($V_{PULSE}$) proportional to the amplitude of the electrical signal 34. Thus, it can be seen that it is possible in this example to vary the stimulation rate by varying the time between ultrasound bursts, to vary the duration of any one stimulation pulse by varying the duration of the ultrasound burst, and to vary the amplitude of the stimulation pulse by varying the amplitude of the transmitted ultrasound waveform. Circuit 21 could be configured to produce a direct current (DC) output or an alternating current (AC) output, or an output with any arbitrary waveform. Varying the use of signal information within the ultrasound transmission for pulse duration, pulse amplitude, and duty cycle would result in any type of burst sequencing or continuous delivery waveform effective for brain stimulation. Using signal information in the ultrasound transmission the resultant waveshape may be a square wave, triangle wave, biphasic wave, multi-phase wave, or the like.

In practice, the amount of acoustic energy received by the implanted receiver-stimulator device will vary with ultrasound attenuation caused by loss in the intervening tissue, with spatial location of the receiver-stimulator device with respect to the transmitted ultrasound beam, as such a beam is typically non-uniform from edge-to-edge, and possibly with orientation (rotation) of the receiver-stimulator device with respect to the first. Such variation would affect the amplitude of the stimulating pulse for a given ultrasound transmit power (acoustic pressure amplitude). This limitation can be overcome by adjusting the ultrasound transmit power until the resultant stimulation waveform is consistent, a technique similar to that used currently to determine stimulation thresholds at the time of cardiac pacemaker implantation. Another approach would be to automatically adjust using sensing and logic within the first device. The first device would periodically sense the electrical output of the receiver-stimulator device and adjust power transmission accordingly to compensate for any change in the system including relative movement between the transmitting and receiving devices. Yet another embodiment for overcoming this limitation is where the transducer incorporated into the receiver-stimulator device is omni-directional in its reception capability. For example, to improve omni-directional sensitivity, the transducer may be spherical in shape or have specific dimensional characteristics relative to the wavelength of the transmitted ultrasound. Alternatively, multiple transducers are disposed at appropriate angles to reduce or eliminate the directional sensitivity of the device.

Figure 6A:
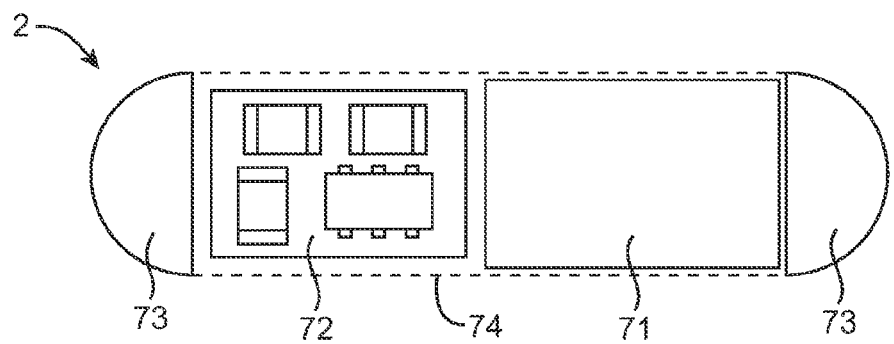
FIGS. 6a, 6b, and 6c are schematic illustrations showing components of the present invention.
Figure 6B:
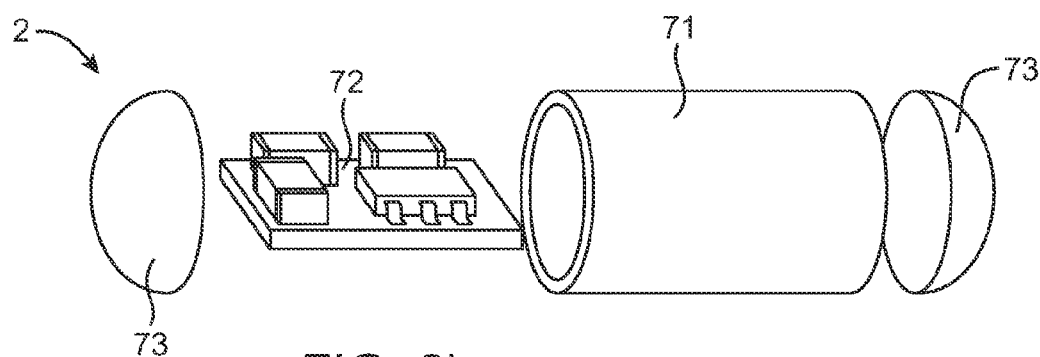
Figure 6C:
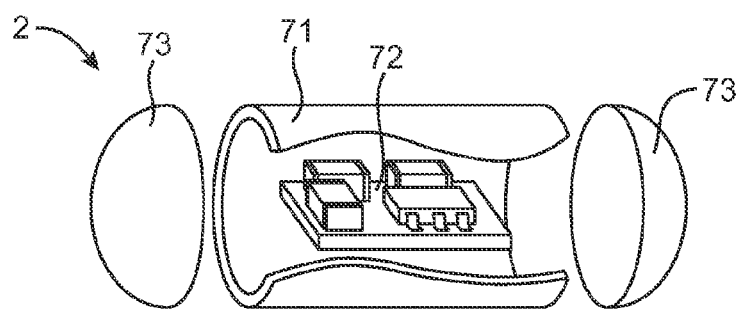

FIGS. 6a through 6c illustrate two embodiments of a small implantable receiver-stimulator of a cylindrical profile, suitable perhaps for placement by stylet or by injection through a hypodermic needle. FIG. 6a shows in plan view and 6b in perspective view such a receiver-stimulator 2 having a hollow, cylindrical ultrasound transducer 71, a circuit assembly 72 comprising the detector, and two electrodes 73 at either end of the assembly. It can be appreciated that any number of electrodes may be adapted to this embodiment. The transducer 71 would be made of an appropriate piezoelectric ceramic material, having two electrical activity contacts deposited on the outer and inner surfaces of the cylinder, respectively. The transducer and circuit would be encapsulated in an electrically insulating but acoustically transparent medium 74. The transducer 71 would be of a rigid piezoelectric material, typically a piezo-ceramic with electrodes deposited on the outer and inner surfaces of the cylinder. The circuit assembly 72 may be fabricated using known surface-mount or hybrid assembly techniques, upon either a fiberglass or ceramic substrate. Stimulation electrodes 73 would be fabricated of material commonly used in implanted electrodes, such as platinum, platinum-iridium, or the like. Necessary electrical wiring between the transducer, circuit board, and electrodes is not shown in these drawings. Typical dimensions of such a device would be 1.5 cm in length and 1.5 mm in diameter, and preferably smaller. Multiple electrodes could be adapted as appendages to the embodiment (not shown) or incorporated into fixation elements such as helical screws or barbs (not shown).

As shown in FIG. 6c, by using hybrid circuit techniques it may be possible to further miniaturize the circuit assembly 72 such that it would fit inside the hollow interior of the transducer 71. This would have the benefit of substantially reducing the length of the finished device.

While exemplary embodiments have been shown and described in detail for purposes of clarity, it will be clear to those of ordinary skill in the art from a reading of the disclosure that various changes in form or detail, modifications, or other alterations to the invention as described may be made without departing from the true scope of the invention in the appended claims. For example, while specific dimensions and materials for the device have been described, it should be appreciated that changes to the dimensions or the specific materials comprising the device will not detract from the inventive concept. Accordingly, all such changes, modifications, and alterations should be seen as within the scope of the disclosure.

What is claimed is:

1. A method for stimulating spine comprising:
   implanting in a body of a patient a controller-transmitter at an implantation site to generate acoustic energy, wherein the controller-transmitter comprises acoustic transducers disposed in a housing and one or more physiological sensors disposed on an external surface of the housing, and wherein the one or more physiological sensors are configured to detect one or more physiological parameters;
   implanting a receiver-stimulator remotely from the controller-transmitter in epidural tissue of the spine of the patient at a spine stimulation site, wherein the receiver-stimulator comprises one or more stimulation electrodes such that the stimulation electrodes lie in electrical communication with the spine stimulation site;
   sensing one or more physiological parameters directly from the body using the one or more physiological sensors;
   generating acoustic energy at the controller-transmitter implantation site using the transducers in the controller-transmitter;
   receiving the acoustic energy at the spine stimulation site using the receiver-stimulator;
   converting the received acoustic energy into an electrical spine stimulation energy output using the receiver-stimulator, wherein the stimulation energy output has at least one of pulse amplitude, pulse duration, duty cycle, and timing based on energy and signal information included in the generated acoustic energy;

delivering the electrical spine stimulation energy output to the spine stimulation site using the one or more stimulation electrodes;

using an external programmer to program one or more settings of the controller-transmitter;

sensing the electrical spine stimulation energy output using the physiological sensors on the housing; and adjusting the acoustic energy transmission from the controller-transmitter to compensate for changes in the electrical spine stimulation energy output of the receiver-stimulator.

2. A method of claim 1 wherein stimulating the spine therapeutically treats patients in pain, the method further comprising:

operating the controller-transmitter to stimulate the spine stimulation site, whereby the patient's pain is alleviated.

3. A method of claim 1 wherein stimulating spine therapeutically treats patients with headache, further comprising:

operating the controller-transmitter such that electrical spine stimulation energy output is generated by the receiver-stimulator at the predetermined spine stimulation site; said predetermined spine stimulation site being selected to treat peripheral nerves consisting of trigeminal ganglion or ganglia, one or more trigeminal nerve, one or more branches of a trigeminal nerve or one or more branches of any of these neural structures;

whereby the headache pain is at least partly alleviated in the patient being treated.

4. A method of claim 1 wherein stimulating spine therapeutically treats patients with pelvic pain, comprising:

operating the controller-transmitter such that electrical spine stimulation energy output is generated by the receiver-stimulator at the predetermined spine stimulation site; said predetermined spine stimulation site being selected to treat peripheral nerves in the sacrum;

whereby the pelvic pain is at least in part alleviated in the patient being treated.

5. A method of claim 1 wherein stimulating spine therapeutically treats patients with spinal injury that causes pain comprising:

operating the controller-transmitter such that electrical spine stimulation energy output is generated by the receiver-stimulator at the predetermined spine stimulation site; said predetermined spine stimulation site being selected to treat any one of the cervical, thoracic, lumbar, sacrum, or coccyx segment of the spine;

whereby the pain is at least in part alleviated in the patient being treated.

6. A method as in claim 1, wherein receiving comprises receiving the energy output at two or more spine stimulation sites.

7. A method as in claim 6, wherein the signal information stimulates different sites sequentially.

8. A method as in claim 6, wherein the signal information stimulates different sites simultaneously.

9. A method as in claim 1, wherein the housing is a hermetically sealed housing.

10. A method as in claim 9, wherein the one or more physiological sensors have a portion within the housing and a portion external to the housing.

11. A method as in claim 10, wherein the one or more physiological sensors are directly connected to a signal processing circuitry of the controller-transmitter.

12. A method as in claim 1, wherein the external programmer transmits a radiofrequency signal and the controller-transmitter comprises circuitry for receiving the radiofrequency signal.

13. A method as in claim 1, wherein the receiver-stimulator consists essentially of an ultrasound transducer which generates a stimulation signal in response to the acoustic energy transmitted by the receiver-stimulator, circuitry which rectifies the stimulation signal, and at least one electrode which delivers the rectified signal as the electrical spine stimulation energy output to spine tissue.

* * * * *